United States Patent [19]
Milo

[11] Patent Number: 5,522,886
[45] Date of Patent: Jun. 4, 1996

[54] HEART VALVE PROSTHESES

[76] Inventor: Simcha Milo, 6a Noga Street, Haifa, 34407, Israel

[21] Appl. No.: 283,390

[22] Filed: Jul. 29, 1994

[51] Int. Cl.⁶ .............................. A61F 2/24; F16K 15/00
[52] U.S. Cl. ............................................. 623/2; 637/527.8
[58] Field of Search ........................... 623/2; 137/512.1, 137/527, 527.8

[56] References Cited

U.S. PATENT DOCUMENTS

| | | | |
|---|---|---|---|
| 215,887 | 5/1879 | Crossman et al. | 137/527.8 |
| 3,448,465 | 7/1966 | Pierce et al. | 137/527.8 |
| 3,945,398 | 3/1976 | Masheder | 137/527.8 |
| 4,306,319 | 12/1981 | Kaster | 623/2 |
| 4,326,304 | 4/1982 | Klawitter | 3/1.5 |
| 4,423,525 | 1/1984 | Vallana et al. | 3/1.5 |
| 4,425,670 | 1/1984 | Figuera | 3/1.5 |
| 4,484,365 | 11/1984 | Murguet et al. | 623/2 |
| 4,512,366 | 4/1985 | Lewis | 137/527.8 |
| 4,689,046 | 8/1987 | Bokros | 623/2 |
| 4,775,378 | 10/1988 | Knoch et al. | 623/2 |
| 4,820,299 | 4/1989 | Philippe et al. | 623/2 |
| 4,872,875 | 10/1989 | Hwang | 623/2 |
| 4,923,465 | 5/1990 | Knoch et al. | 623/2 |
| 5,064,432 | 11/1991 | Reif | 623/2 |
| 5,108,425 | 4/1992 | Hwang | 623/2 |
| 5,156,600 | 10/1992 | Young | 604/247 |
| 5,207,707 | 5/1993 | Gourley | 623/2 |
| 5,314,467 | 5/1994 | Shu | 623/2 |
| 5,326,372 | 7/1994 | Mhatre et al. | 623/2 |

FOREIGN PATENT DOCUMENTS

8802247  4/1988  WIPO ........................... 623/2

*Primary Examiner*—David Isabella
*Assistant Examiner*—Laura Fossum
*Attorney, Agent, or Firm*—Fitch, Even, Tabin & Flannery

[57] ABSTRACT

Check valves for fluid flow, particularly for use as replacement heart valves, employ annular valve bodies with hinge arrangements which support one or more occluders for movement between open and closed orientations. Illustrated are single occluder and tri-leaflet valves in which each occluder is pivotally mounted by pegs of oval cross-section that protrude from opposite lateral surfaces and are received in sockets formed in the interior surface of an annular valve body. One valve is constructed with a unique shape for advantageous employment in the mitral or tricuspid position. The inflow surface of each occluder is formed with a convex surface region, preferably of cycloidal shape, at a downstream location preferably adjacent the downstream edge and spaced a substantial distance from the pivot axis. Upon initial reverse flow of blood, a low pressure region forms which creates a suction effect causing immediate initiation of pivoting movement of the occluder toward the center of the flow passageway. This force is magnified by the moment arm resulting from the spacing and assures the prompt beginning of closing movement, which is swiftly completed as a result of the strategic location of a hollow region on the outflow surface of the cycloid section which is effectively impacted by the full force of the reverse flow of blood.

20 Claims, 7 Drawing Sheets

HEART VALVE PROSTHESES

FIELD OF THE INVENTION

The present invention relates to mechanical check valves for fluid flow, particularly heart valve prostheses, and more particularly, it relates to improved prosthetic heart valves having one or more valve members or occluders which pivots generally about an eccentric axes moving between a closed position and an open position in a manner which provides a relatively large unobstructed center flow passageway.

BACKGROUND OF THE INVENTION

A wide variety of heart valve prostheses have been developed over the past several decades to serve as replacements for defective natural valves; they operate hemodynamically, as fluid check valves, in conjunction with the pumping action of the heart. These mechanical heart valves have variously had valve bodies which are designed to function together with either a valve member in the form of a single occluder or with two, three or more occluders or leaflets; in any event, the valve members generally pivot along eccentric axes (or both pivot and translate) to open and close a blood flow passageway defined by the valve body.

U.S. Pat. No. 4,689,046 (Bokros) shows a version of a bileaflet heart valve wherein each leaflet has an ear of specific shape extending from each lateral edge, which ear pivots in a recess of complementary shape. The valve is generally referred to as a side flow valve because there is a greater flow area in the regions lying between each leaflet and the surrounding valve body than in the central region between the two leaflets.

U.S. Pat. No. 4,326,304 (Klawitter) illustrates a single occluder valve wherein the occluder is made of substantially uniform thickness having a concave-convex configuration and a generally elliptical periphery to fit within a valve body having a passageway that has a generally right circular cylindrical configuration except for a pair of opposed flat sidewalls where the pivot mechanism is located. The occluder is located generally centrally of the flow passageway, and it is oriented in its open position, as shown, at an angle of about 10°–15° from the valve body centerline to assure prompt and reliable closing.

U.S. Pat. No. 4,425,670 (Figuera) discloses another version of a heart valve prosthesis which has a single occluder of irregular shape. The occluder is also located generally centrally within the valve passageway and is guided in its pivoting movement by pair of pegs that extend outward from the wall of the valve body and are received in cavities provided along the lateral edges of the occluder.

U.S. Pat. No. 4,775,378 (Knoch et al.) discloses a heart valve prosthesis employing a single occluder having a shape, along its centerline, generally that of an S-shaped curve. The occluder has an upstream section wherein the pivot axis is located, which section has a convex surface that faces downstream in the closed position. It is oriented at maximum opening angle of about 65°–75° and thus occupies a significant portion of the center of the valve passageway. U.S. Pat. No. 4,846,830 discloses a bileaflet valve having a pair of leaflets of generally similar curvature to the foregoing.

U.S. Pat. No. 4,923,465 (Knoch et al.) shows a cardiac valve prosthesis wherein a single occluder is journaled by a pair of laterally extending pins that are received in holes that extend completely through the wall of the valve body. The occluder itself has a composite S-shaped curvature. As shown in FIGS. 2 and 3, the occluder obscures a large portion of the central region of the valve passageway in the open position, likely creating a region of dead flow downstream therefrom.

U.S. Pat. No. 5,108,425 to Hwang discloses a bileaflet valve employing a pair of leaflets having generally flat upstream sections and complex curvature in their downstream sections to promote aerodynamic performance. U.S. Pat. No. 4,872,875 shows an earlier version of such a bileaflet valve.

U.S. Pat. No. 4,423,525 (Vallana et al.) shows a single occluder valve where the occluder is free to rotate about its central axis and is guided in its pivoting action by protrusions that extend from the annular valve body. If the occluder were to be oriented parallel to the central axis, as illustrated in FIG. 2, it would not be assured to close promptly and reliably.

U.S. Pat. No. 5,314,467 shows a bileaflet valve having leaflets of a composite curvature which both pivot and translate in moving between their open and closed positions, guided by recesses in the sidewall of the valve body that receive ears extending from the lateral edges of the leaflets. The guiding recesses are described as each having one epicycloid-serpentine shaped sidewall and one concave sidewall.

U.S. Pat. No. 4,820,299 discloses a tri-leaflet cardiac valve having three "flaps" that are essentially 120° segments of relatively smooth curvature. Pivoting motion is controlled by spurs 17, 18 and 19, the central one of which interengages with a stirrup 16 and magnetic masses at the corners of the flaps can be used to assist movement.

U.S. Pat. No. 5,207,707 discloses a tri-leaflet valve wherein the leaflets have an essentially flat main body which meet at a central point in the closed position. The pivot recesses are located in three interior protrusions and constitute curved grooves that accommodate ears 74 that are fashioned from the canted edge sections of each leaflet. The valve presents a generally triangular shaped special opening in its open position; however, there is no guarantee that the leaflets will promptly close or will simultaneously close.

Commercially developed heart valves have employed several designs similar to those set forth in various of the aforementioned U.S. patents; however, all such commercially feasible designs are felt by those working in this field to have various shortcomings compared to the fluid dynamic performance of the natural heart valves for which they are substituting. Further improvements are felt necessary particularly with respect to fluid flow rate and pressure drop through the valve body, to reducing the volume of blood which regurgitates upon reversal of flow, e.g., at the end of a pumping stroke, to the ability of the valve to operate in a thrombus-free fashion for the life of the patient, and to the ability to avoid regions of turbulence and potential blood damage. As a result, improvements in valve construction have continued to be sought with the objective of creating mechanical valves with flow characteristics such that there is minimum resistance to blood flow and/or damage to blood itself, which valves close promptly upon the termination of the pumping stroke with only low regurgitation.

SUMMARY OF THE INVENTION

The present invention provides mechanical fluid flow check valves exhibiting the aforementioned desirable characteristics wherein one or more valve members or occluders, guided by laterally disposed, eccentrically located pivot or hinge arrangements are supported within a valve body so as to provide an unobstructed central flow passageway of relatively large cross-sectional area, preferably equal to at least about 80% of the cross-sectional area of the valve passageway. A prosthetic valve is provided having a shape and arrangement which makes it particularly well suited to replace defective mitral and tricuspid valves.

The valve body and occluder(s) are preferably constructed so that the occluder is oriented substantially parallel to the centerline through the valve body in the open position so as to provide low resistance to flow, yet it will close promptly upon the reversal of fluid flow, particularly at the end of a pumping stroke of the human heart to minimize regurgitant blood flow through such a prosthetic valve. Very generally, this improved arrangement utilizes an occluder(s) that has a main body portion of uniform wall thickness which is generally a section of a tube having a concave inflow surface, which may be generally cylindrical, except for a downstream section extending to the downstream edge; this downstream section is convex, preferably having a cycloidal surface. Placement of this cycloidal section at this location has a dramatic effect in promptly initiating closing pivotal movement of the occluder(s), which is enhanced further by the regurgitant blood flow pressing directly upon the transversely aligned concave rear surface of this downstream section.

DETAILED DESCRIPTION OF THE PREFERRED EMBODIMENTS

Figure 1:
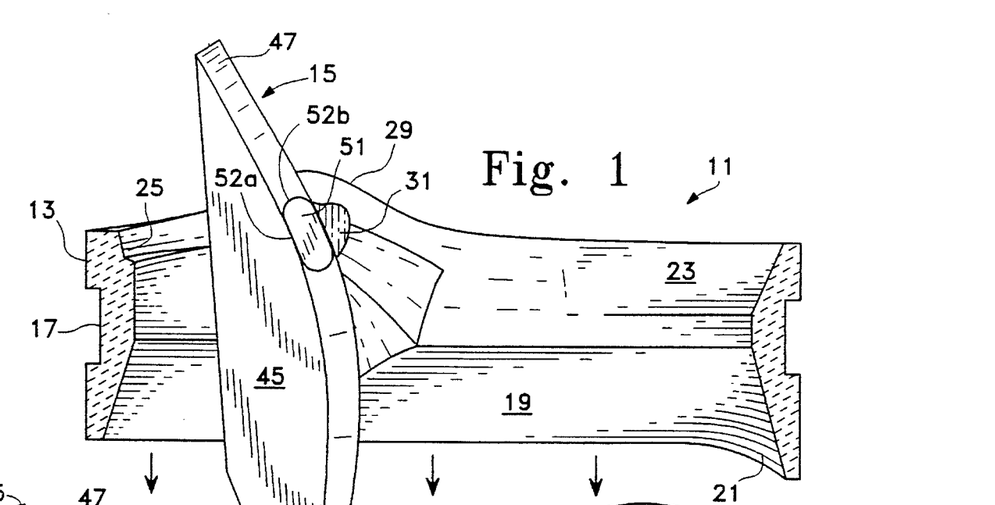
FIG. 1 is a sectional view of a single occluder valve embodying various features of the invention especially designed for replacement of an aortic valve, with the occluder being shown in elevation in the open position.
Figures 4, 5A:
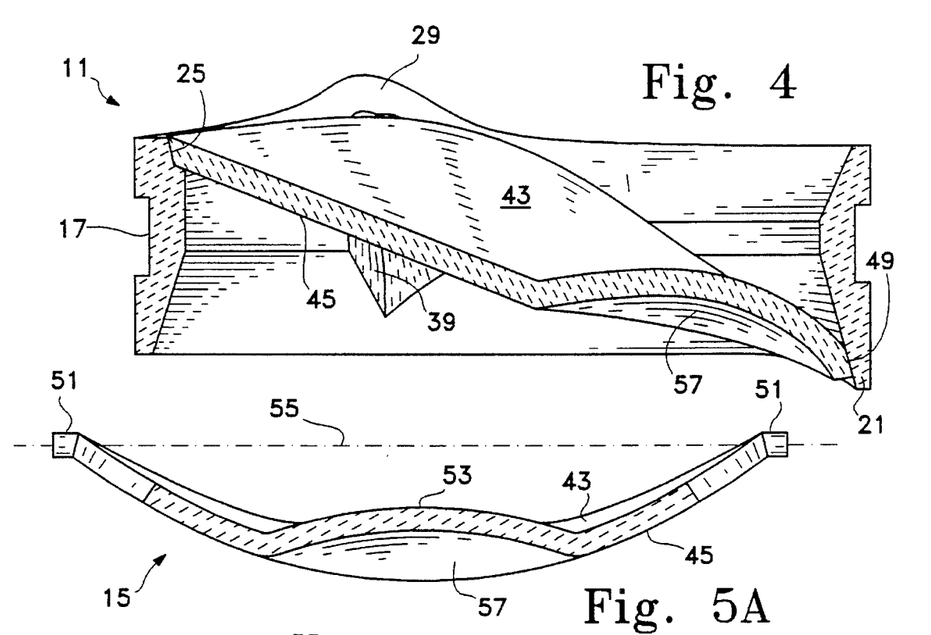
FIG. 4 is a sectional view generally similar to FIG. 1 taken through the valve with the occluder in the closed position.
FIG. 5A is a sectional view, enlarged in size, taken generally along the line 5A—5A of FIG. 5.

Illustrated in FIG. 1 is a prosthetic heart valve 11 which is particularly designed for replacement of an aortic valve. The heart valve 11 includes an annular valve body 13 and a single occluder 15. The annular valve body 13 has an outer surface which is generally that of a right circular cylinder in which has been cut a generally centrally located groove 17; the groove is designed to facilitate the connection of the annular valve body 13 to a suture ring (not shown) as is well known in this art. The interior surface of the valve body 13 is also of generally circular configuration; it defines the valve passageway which has an axial centerline extending upstream and downstream. As can be seen in FIG. 1, it is generally at its smallest diameter in the central region except for those locations where the interior wall is cut away to provide clearance for the pivoting occluder 15. Normal blood flow through the valve is downward with respect to FIG. 1, as indicated by the arrows just below the valve body, and the interior surface of the valve body has a downstream end portion 19 that is frustoconical. Preferably a partial skirt extension 21 is provided in the region of the valve body distal from the pivot, in order to provide a seat for the entire periphery of the occluder in the closed position, as best seen in FIG. 4, without uniformly extending the length of the entire valve body 13, which of course is an option. The interior surface also has an upstream region 23 that is also preferably frustoconical, and it contains an arcuate groove 25 which provides a seat for the upstream edge of the occluder 15 in the closed position.

The upstream edge surface 27 of the valve body 13 is generally planar except for two bulges or prominences 29 where the valve body extends above its otherwise planar upstream edge to accommodate the hinge mechanism which interconnects the valve body and the occluder, again without uniformly extending the height of the entire valve body, which of course is an option as indicated hereinbefore. The valve body 13 can be made of any suitable material; however, it is preferably made of a suitable substrate, such as isotropic graphite, coated with pyrolytic carbon, or of all pyrolytic carbon. These two materials are well known in the heart valve industry as materials of choice for the past two decades, because of the durability and nonthrombogenecity of pyrocarbon.

Figure 2:
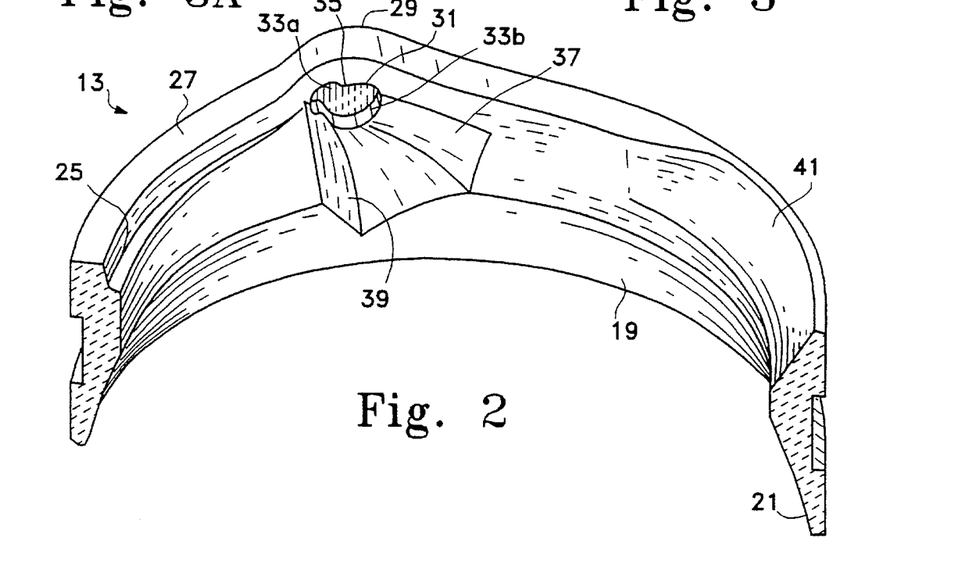
FIG. 2 is a perspective view of the valve body shown in FIG. 1 with the occluder removed.

As best seen in FIG. 2, a pair of recesses or sockets 31 are provided in the interior surface of the valve body 13; these sockets are located in opposite regions of the valve body and are aligned to provide a pivot axis for the occluder. Each socket 31 is formed to include a pair of lobes 33a and 33b which are generally separated by projections 35 that extend into the socket and serve partially as fulcrums to direct the pivoting movement of the occluder, as explained in detail hereinafter. A relief 37 is cut in the interior surface of the valve body to provide clearance for the lateral periphery of the occluder 15 as it swings from the closed to the open position and vice-versa. The relief 37 is contoured so as to create an axially extending surface 39 which operates as a stop and thereby to determine the precise orientation of the occluder in the maximum open position, as shown in FIG. 1. A further relief 41 is provided in the upstream region 23 of the interior surface above the skirt 21 to generally improve fluid flow through the interior passageway of the valve.

Figure 3:
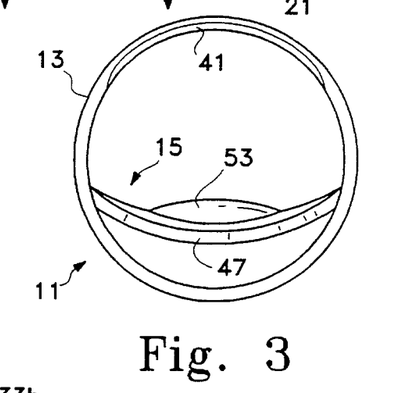
FIG. 3 is a top view, reduced in size, of the valve shown in FIG. 1 in the open position.
Figure 3A:
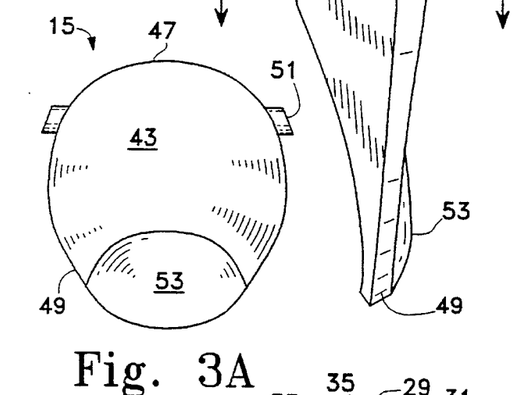
FIG. 3A is a front view, reduced in size, showing the inflow surface of the occluder illustrated in FIG. 1.

As best seen perhaps in FIGS. 3 and 5A, the occluder 15 has a main body portion which is generally tubular in shape, being essentially a section of a hollow right circular cylinder of uniform wall thickness. The occluder 15 has a concave inflow surface 43, which constitutes the major upstream portion of the occluder, and which is accordingly curved in the plane perpendicular to the axial centerline having a substantially constant radius of curvature although the radius may vary if desired. The opposite surface of the upstream section constitutes a convex outflow surface 45. The periphery of the occluder 15 is formed with an annular upstream edge 47 of arcuate shape proportioned to be accommodated in juxtaposition with the seat provided by the arcuate groove 25 in the upstream surface of the valve body 13 and with a downstream major arcuate edge 49, which seats generally along the frustoconical downstream surface 19 of the valve body in the closed position.

Figure 5:
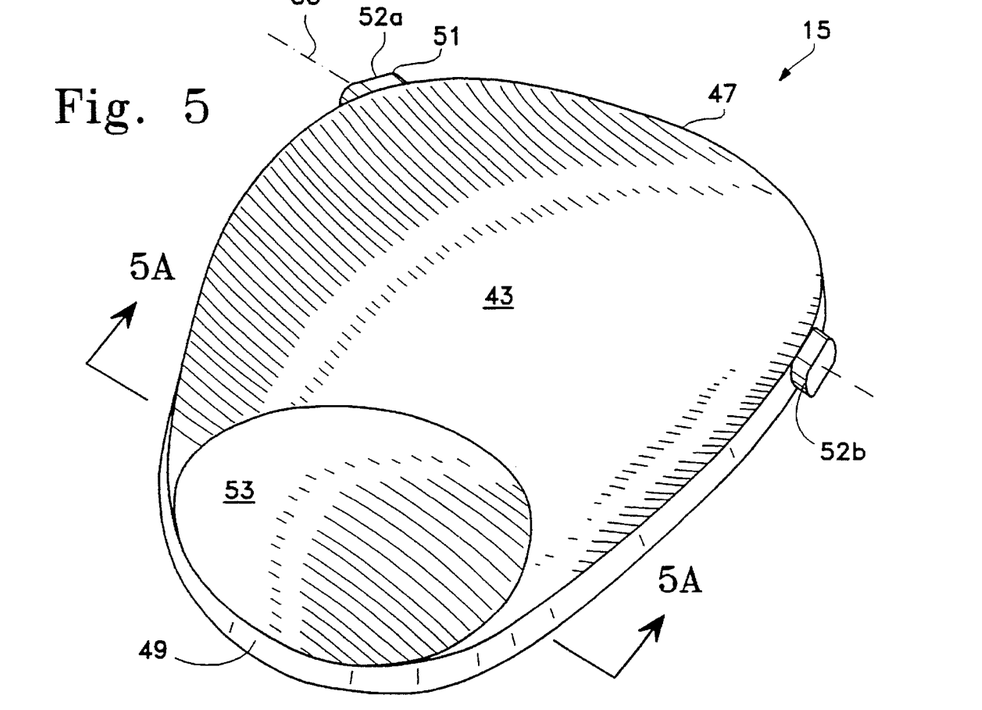
FIG. 5 is a perspective view enlarged in size looking at the inflow surface of the occluder of the valve of FIG. 1.

Protruding laterally from the edges of the occluder 15 are a pair of oval pivots or pegs 51, which are each formed with a pair of flat parallel surfaces 52a and a pair of convex end surfaces 52b. The key to the effective functioning of the occluder 15 is the provision of a downstream convex region 53 in the inflow surface, which is curved in the plane containing the axial centerline of the valve body that bisects the occluder and in planes parallel thereto. The radius of curvature is preferably changing in a uniform manner, and it more preferably is of cycloidal shape. At any point along its curvature in such a plane, the radius of curvature is preferably generally shorter than that of said upstream section. This surface region 53 is located as far as possible from the pivot axis 55 which is defined by the oval pegs 51, as best seen in FIGS. 5 and 5A, and it extends downstream to the major arcuate edge 49 of the occluder. As best seen in FIG. 5A, the occluder 15 is preferably of uniform thickness throughout this region, and therefore a spoon-like hollow or recess 57 is provided in the downstream region of the outflow surface of the occluder, which hollow functions along with the convex surface to initiate prompt closing of the valve upon the reversal of blood flow.

A valve body 13 made of pyrocarbon-coated graphite has sufficient resiliency to allow it to be deformed to spread the sidewalls containing the sockets 31 sufficiently outward to accept the pegs 51 of the occluder 15 and thus operatively mate it with the valve body. With blood flowing downward through the valve in the open position as depicted in FIGS. 1 and 3, it can be seen that the arrangement provides an unobstructed, single, central passageway equal to about 85% of the cross-sectional area through the valve body measured in a plane perpendicular to the axial centerline, a term which is sometimes spoken of as effective orifice area (EOA). Preferably, the EOA is at least about 65% for this valve design, and more preferably it is at least about 80%. The generally cylindrical surfaces of the upstream portion of the occluder are rectilinear surfaces, and in this orientation, they are aligned at an angle of about 5% from the axial centerline through the annular valve body 13. As indicated before, this orientation is determined by the location of the stop surface 39 which engages the edge of the occluder. The occluder 15 could be oriented precisely parallel to the centerline if desired; however, testing has generally shown that an occluder of this configuration has a tendency to seek such an orientation about 5% from the centerline under most flow conditions. Thus, in the illustrated orientation, the occluder is considered to provide minimum obstruction to the downstream flow of blood through the valve 11.

Upon the reversal of blood flow through the valve as a result of the heart entering its next cycle, there will be a backflow of blood upstream through the valve 11, i.e. upward through the valve as oriented in FIG. 1. It is important that a mechanical heart valve close promptly so as to minimize the amount of regurgitation of blood at the end of each cycle, and in the valve 11, the presence of the convex cycloidal surface 53 assures prompt closing occurs. This convex surface, as can be seen in FIG. 4, is curved in the plane which bisects the occluder 15 and includes the centerline axis of the valve (which is herein termed the centerline plane), and its presence requires the blood flowing upward past this curved surface to flow at a higher rate of speed than the blood flowing along the remainder of the rectilinear surface of the occluder. Moreover, it has been found that in order to get maximal acceleration of such particles of liquid in this region, a convex section having a cycloidal shape should be used. Maximum acceleration of the liquid particles causes maximum pressure difference, i.e. suction, along this surface of the leaflet at the beginning of the reverse flow of blood. This pressure difference or suction at a location between the inflow surface of the leaflet and the centerline of the valve causes the application of a transverse force in this convex region which causes the occluder to swing toward the midstream or axial centerline, i.e. initiating pivoting toward its closed orientation. Moreover, by locating the cycloidal surface 53 spaced as far from the pivot axis 55 as feasible, the maximum moment arm is obtained, which magnifies the effect of this force being applied to the occluder. Furthermore, as soon as the pivoting movement is promptly initiated as a result of the pressure drop, the backflowing bloodstream impacts squarely against the surface of the spoon-like hollow 57 on the outflow surface of the occluder, and this direct impingement of the blood flow against a transverse surface assures the swift swinging movement of the occluder to the closed position shown in FIG. 4.

As noted above, the surface of the convex section 53 is preferably cycloidal. By cycloidal is meant that it can have the shape of a cycloid or of an epicycloid or a prolate or curtate version of either. The shape of a common cycloid is a generally preferred shape, which is a curve traced by a point on the radius of a circle which rolls along a straight line in a plane. In this case, the center of the convex region is the central plane which bisects the occluder, i.e. the centerline plane, and the generating point is on the circumference of the circle which rolls along a line in this plane. The curvature of the convex region can be the same laterally across the downstream section of the occluder, or if desired, the shape of the cycloid can vary by gradually decreasing the length of the generating arm (from that of the full radius) as the distance increases between the plane in which the curve is generated outward from the centerline plane, as a result of which there will be some slight curvature of the convex surface in the direction perpendicular to the centerline of the occluder. Likewise, although the cycloid is preferably generated with an inclination angle of 0°, i.e. so that the plane of reference is the plane of the rectilinear upstream surface of the occluder, generally, an inclination angle up to about 10° on either side of 0° can be employed. Likewise, although a flat plane of reference is preferred so that the curvature of the surface is that of a cycloid, the reference can be a circle of large diameter so that the curvature of the downstream inflow surface region 53 will be that of an epicycloid; such may be preferred in an instance where the upstream section of the occluder is not rectilinear in the upstream-downstream direction but instead has some curvature in the upstream-downstream direction in addition to its distinct concave curvature in the transverse direction, which is best seen in FIG. 3. By employing a prolate or a curate cycloidal curvature, where the generating arm is either shorter than or longer than the radius of the generating circle, it may be possible to optimize streamlined flow along the occluder's inflow surface with minimal pressure drop through the valve, while still accomplishing prompt closing and low regurgitation.

Figures 6, 6A, 7:
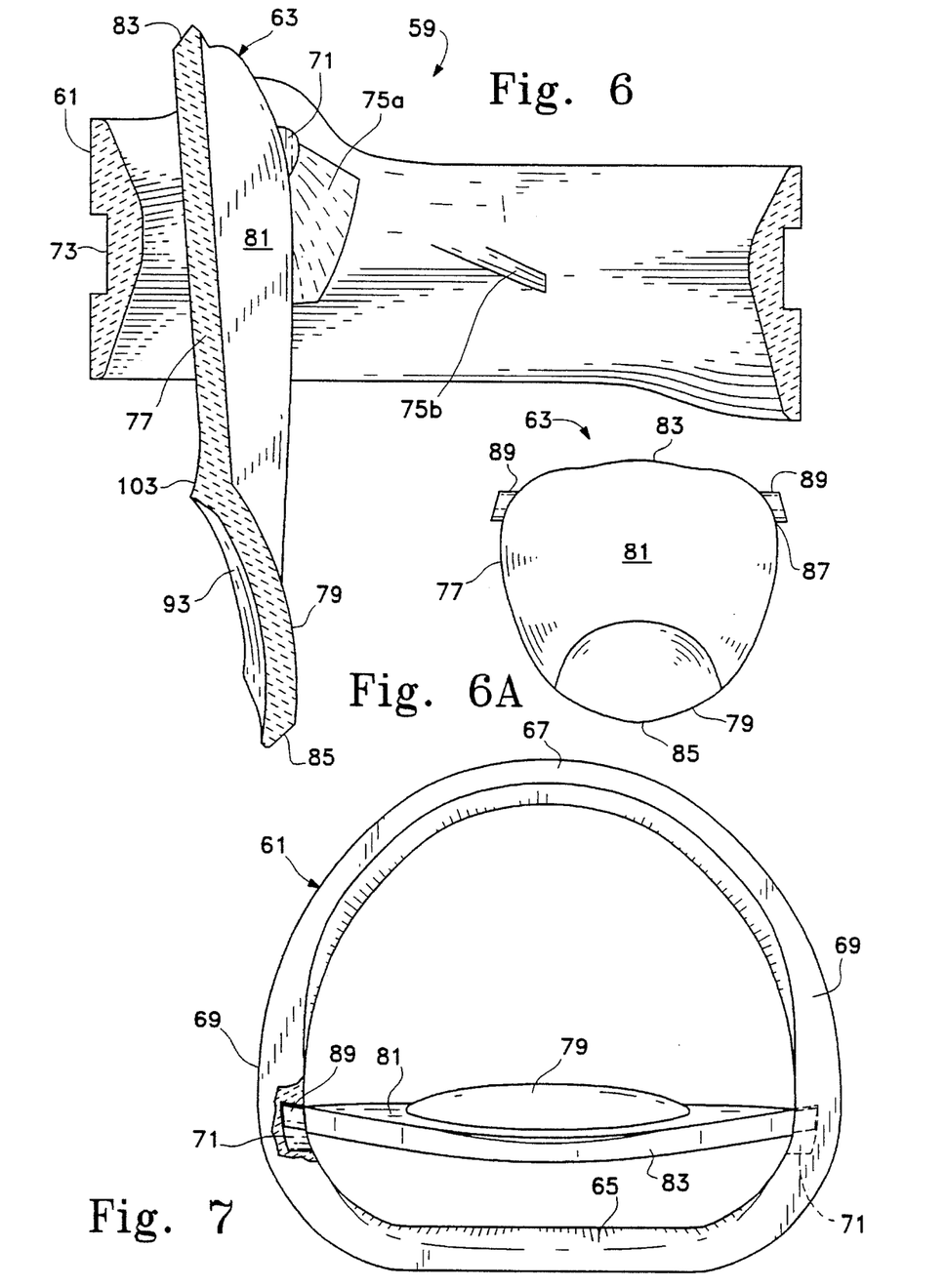
FIG. 6 is a sectional view of an alternative embodiment of a single occluder heart valve, particularly designed for replacement of a mitral or a tricuspid valve, shown with the occluder in the open position.
FIG. 6A is a front view, reduced in size, showing the inflow surface of the occluder of the valve of FIG. 6.
FIG. 7 is a top view, with a portion broken away and shown in section, of the valve of FIG. 6 in the open position.

Illustrated in FIGS. 6 through 10 is an alternative embodiment of a prosthetic heart valve 59 which is particularly designed for replacement of a heart valve in the mitral position. The valve 59 includes an annular valve body 61 and a single occluder 63, both of which can be made of pyrocarbon or pyrocarbon-coated graphite as was the case for the valve 11. A significant difference between the valve 59 and the valve 11 is that the valve body 61 is noncircular in shape, as best seen in FIG. 7. Although it is annular, having a wall that has about the same maximum thickness about its entire periphery, the valve body 61 is noncircular in plan view; it is shaped in a manner to provide particularly efficient flow in the mitral or tricuspid position as a result of having a generally straight minor wall section 65 and a substantially semicircular major wall section 67, having the general shape of about ½ of a short, hollow cylinder, as best seen in plan in FIG. 7. These two wall sections are joined by arcuate connecting wall sections 69 in which are located a pair of sockets 71 which form a part of the hinge arrangement. The valve body 61 has the usual groove 73 in its exterior surface to facilitate connection to a suture ring of appropriate size and shape to allow the prosthetic valve to be sutured to the wall of the heart cavity from which the defective natural valve has been excised. In addition to the valve body 61 being formed with upstream and downstream frustoconical interior surface regions, the interior surface is also provided with reliefs 75a and 75b which provide clearance for the edge of the occluder as it moves from the open position shown in FIG. 6 to the closed position shown in FIG. 8.

Because the shape of the valve 59 mimics the shape of the natural mitral valve, replacement of a defective mitral or tricuspid valve can be accomplished with removal of a minimum amount of the heart wall by using a prosthetic valve of very similar geometry which is well-accommodated within the heart and constitutes a particularly advantageous physiological solution. However, in addition to this advantage, the flow pattern of the blood through the valve 59 when located in the mitral or the tricuspid position is further improved as explained hereinafter.

The occluder 63 is constructed so as to have a shape which closes the noncircular cross section, irregular opening through the valve passageway provided by the interior surface of the valve body 61. The main body of the occluder 63 has an upstream section 77 and a downstream section 79. The inflow surface 81 of the occluder is concave in the upstream section 77, being curved in a plane perpendicular to the axial centerline, and it is convex in the downstream section 79, in this respect resembling the occluder 15 of FIGS. 1–5. The occluder 63 has a minor upstream edge 83 that is generally straight but is contoured so as to provide a seal against the upstream entrance region of the interior frustoconical surface of the valve body 61. The occluder 63 likewise has a major downstream arcuate edge 85 which is nearly semi-elliptical in shape and which is similarly contoured so as to provide a seal when located in juxtaposition with the frustoconical interior surface of the downstream region of the valve body 61.

A pair of lateral, arcuate, connecting sections 87 are located between the upstream and downstream edges, and a pair of oval cross section pivots or pegs 89 extend outwardly from the lateral arcuate sections 87, which pegs are coaxial with each other. As best seen in FIG. 6A, the occluder 63 has its widest lateral dimension in the region just downstream from the location of the oval pegs, and the relief 75a cut in the interior surface of the valve body 61 provides clearance for this wide region of the occluder to pivot upward from the open orientation shown in FIG. 6 to the closed orientation shown in FIG. 8 as explained hereinafter. The relief 75b provides further clearance at a location just slightly downstream therefrom.

Figure 8:
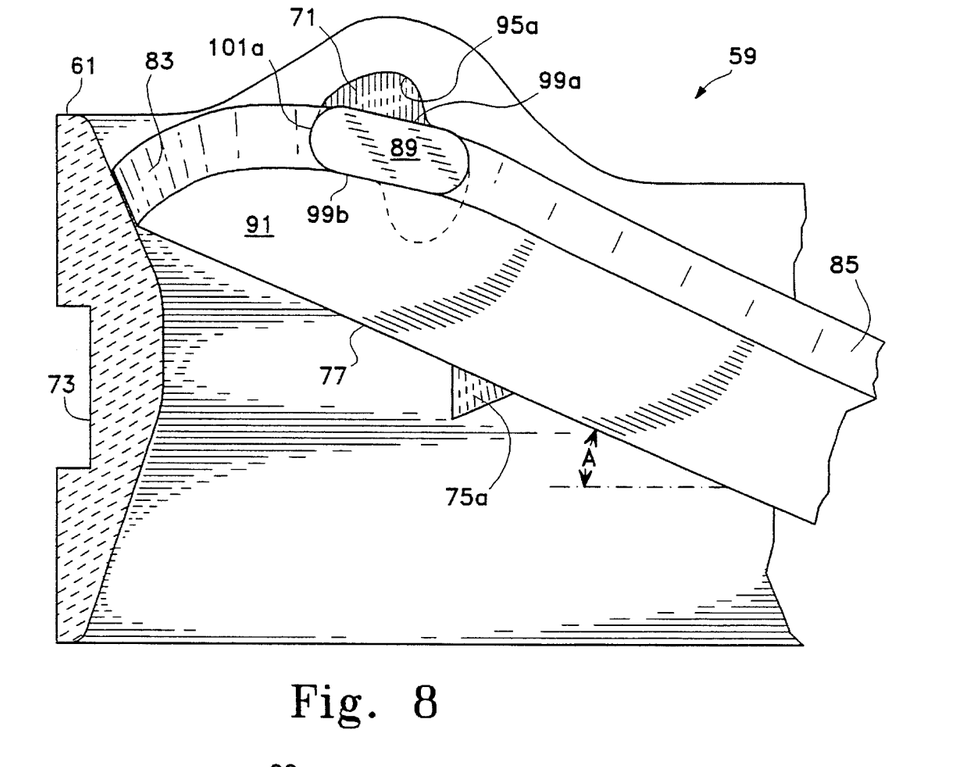
FIG. 8 is an enlarged fragmentary sectional view, with the occluder shown in elevation, of the valve of FIG. 6 shown in the closed position.

As best seen perhaps in FIGS. 6, 7 and 8, the inflow surface 81 of the upstream section 77 of the occluder is concave. The inflow surface 81 may be slightly curved or rectilinear in the axial direction when in the open orientation, as was the corresponding surface of the occluder 15, and as seen in FIGS. 6 and 7, the inflow surface 81 is preferably generally rectilinear in the upstream-downstream direction. However, because of the occluder's irregular shape, its radius of curvature in the transverse plane may preferably vary across the width of the occluder, i.e. it need not be a section of a tube of circular cross-section. The inflow surface of the downstream section 79 of the occluder is convex, being curved in the axial centerline plane which bisects the occluder, and as explained hereinbefore, it is preferably cycloidal. As best seen in FIG. 6, the cycloidal region extends to the downstream edge 85 of the occluder and has the same effect, at the instant of beginning backflow of blood, as described hereinbefore. Again, the occluder 63 is of generally uniform thickness throughout. As a result, its upstream section 77 has an outflow surface 91 which is convex, and the outflow surface of the downstream section 79, as best seen in FIG. 6, is that of a spoon-like hollow region 93. As described hereinbefore with respect to the occluder 15, the hollow 93 provides a surface upon which there is substantially direct impingement by the blood which assures swift pivoting of the occluder to the closed position and thus limits the amount of regurgitation of blood to an acceptably low level.

Figure 9:
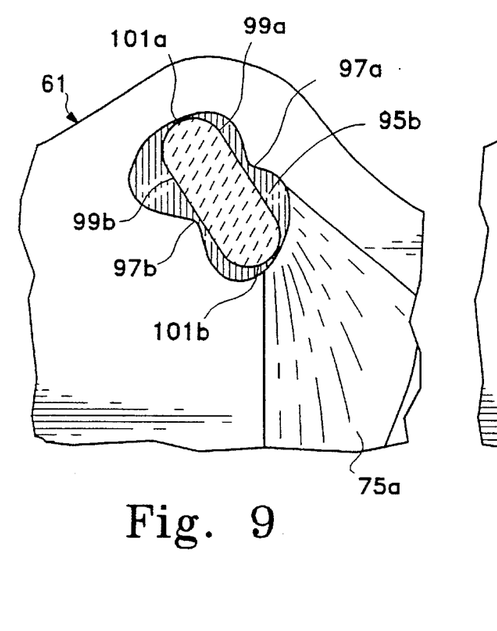
FIGS. 9 and 10 are enlarged fragmentary diagrammatic views showing a portion of the valve body of the valve of FIG. 6 to illustrate a socket located in the interior surface in combination with a representation of an oval protrusion extending laterally from each side of the occluder, shown in FIG. 9 as is movement occurring from the closed position depicted in FIG. 8 to the open position depicted in FIG. 10.
Figure 10:
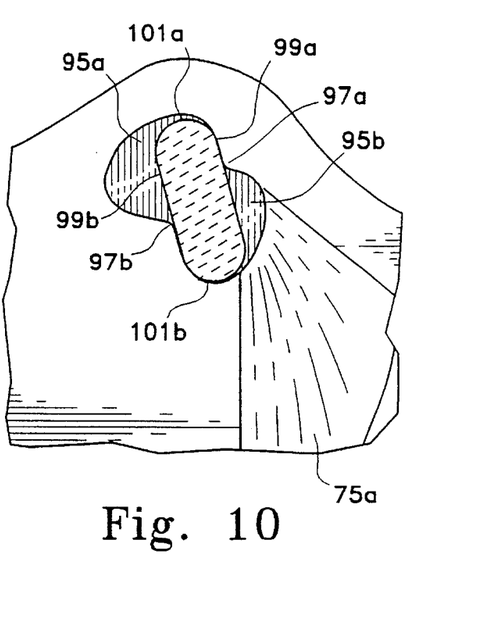

The valve body 61, as explained hereinbefore, is made of a pyrocarbon-coated graphite substrate or the like which has sufficient resiliency to permit it to be distended sufficiently so that the oval pegs 89 of the occluder can be fit into the sockets 71 that are designed to receive them. The sockets 71 are formed with a pair of lobes 95a and 95b, which are referred to herein as an upstream lobe 95a and a downstream lobe 95b; the function of the hinge arrangement in the heart valves 11 and 59 is explained hereinafter in detail with respect to the sockets 71 and the oval pegs 89, by making particular reference to diagrammatic views 9 and 10. The lobes 95a and 95b are separated by projections 97a and 97b which extend toward each other, and the oval pegs 89 are formed with parallel flat surfaces 99a and 99b that are interconnected by convex end surfaces 101a and 101b of generally semi-circular cross-sectional configuration.

FIG. 8 shows the valve 59 closed, with the occluder 63 in its closed orientation blocking reverse or upstream blood flow through the valve. In this orientation, the outflow surface 91 of the upstream section 77 of the occluder is oriented at an angle A (FIG. 8) of about 24° to the horizontal plane, i.e. the plane which is perpendicular to the centerline of the valve passageway. In this closed orientation, the upstream edge 83 of the occluder lies in juxtaposed sealing arrangement with the interior surface of the valve body 61. The downstream edge 85 of the occluder is likewise located in juxtaposition with the interior surface of the valve body 61, as are the connecting sections 87. Thus, there is created a seal about the entire periphery of the occluder except for the region of the socket 71. The proportioning of the pegs 89 and the sockets 71 is such that there is a controlled leakage through this region when the valve is in the closed position so as to create a cleansing flow as generally known in this art.

Because of the sealing arrangement between the edge of the occluder 63 and the interior surface of the valve body 61, there is only minimal force of the upper surfaces 99a of the pegs 89 against the corresponding surfaces of the projections 97a so as to minimize wear in this area when the valve is in the closed position and the forces bearing against the occluder are at their highest. As soon as reverse flow ends and the normal flow through the valve is to resume, the force of the blood against the inflow surface 81 of the occluder initiates the opening movement thereof. More particularly, such downstream-directed force on the occluder causes the flat surface 99b of the oval pegs 89 to engage the vertex of the projection 97b, which serves as a fulcrum about which pivoting and translation occurs, causing the occluder to begin to pivot clockwise as viewed in FIG. 8.

As the opening pivoting begins, the normal downstream flow of blood through the valve passageway defined by the valve body 61 travels along the inflow surface 81 of the occluder, creating a downstream drag on the occluder which causes some translation of the occluder to occur, as permitted by the sockets 71, in addition to the rotation about the pivot axis. Thus, as a part of this opening movement, pivoting of the occluder generally occurs about the vertex of the projection 97b as a fulcrum, and because of this slight translational movement, the pivot axis of the occluder shifts slightly from the beginning to the end of the clockwise pivoting. As a further result of this translation, the convex end surfaces 101b of the pegs slide along the interior curved surface of the downstream lobe 95b of the socket. Because the radius of curvature of the convex end surface 101b is smaller than the changing radii of curvature of the lobe 95b, it can be seen that contact between the two surfaces will be generally along a line that will be moving as the oval pegs rotate clockwise, starting at the orientation shown in FIG. 8, moving through the orientation shown in FIG. 9, and ending at the open position orientation shown in FIG. 10.

With the occluder in the open position, the upstream section of the flat surface 99a of each oval peg (FIG. 10) will be in juxtaposition with the corresponding flat surface section of the projection 97a in the upstream lobe 95a, and the downstream section of the flat surface 99b will be similarly in juxtaposition with the corresponding flat surface of the projection 97b in the downstream lobe 95b. Because of the drag of the flowing bloodstream against the surfaces of the occluder 63, the convex end surface 101b will be seated against the curved concave surface of the downstream lobe 95b of the socket. Thus, in this orientation, the sockets 71 can be used to define stops which will position the occluder in its desired full open position; however, the edge portion of the relief 75a axially below the socket is preferably contoured to create a stop surface against which the corresponding edge of the outflow surface 91 of the occluder abuts.

Upon the reversal of blood flow through the mitral valve 59 as a result of the beginning of the next cycle of the pumping of the heart, the backflow of blood in the region of the convex cycloidal surface of the downstream section 79 causes acceleration of the particles of blood and results in a low pressure region at this location. This creates a force normal to the surface of the cycloidal region toward midstream which, as viewed in FIG. 6, causes the occluder to rotate in a counterclockwise direction about the pivot axis defined by the oval pegs 89. Again, because the cycloidal section extends to the downstream edge 85 of the occluder, this closing force is magnified as a result of its acting through a long moment arm. In addition, as shown in FIG. 6, the outflow surface of the occluder is constructed so as to have an arcuate ridge 103 at the line of demarcation between the convex upstream section 77 and the hollow 93, which ridge projects beyond or past the "plane" of the rectilinear outflow surface of the occluder. This ridge 103 has the effect of extending the hollow 93 further outward into the path of the reverse flow of blood; thus, it establishes impact between the bloodstream and the generally transverse surface provided by the hollow 93 at a slightly earlier time during closing rotation. Closing is promptly initiated as a result of the pressure drop described hereinbefore and, coupled with the ridge 103, contributes to minimizing the amount of regurgitation of blood which occurs as the occluder swiftly pivots to its closed position shown in FIG. 8.

With respect to the hinge arrangement, during the closing movement of the occluder, the drag against the surfaces of the occluder 63 causes the convex end surfaces 101a of the pegs 89 to engage the concave surfaces of the upstream lobes 95a of the sockets and also causes the flat surfaces 99a to engage the projections 97a at the vertex thereof. Thus, pivoting occurs about the vertex of the projection 97a as a fulcrum with the pivot axis changing slightly as the oval pegs 89 translate slowly along the vertex, guided by the interengagement between the convex end surfaces 101a of the pegs and the concave interior surface of the upstream lobes 95a. Again, as explained hereinbefore, because the radius of curvature of the convex end surface 101a is smaller than the changing radii of curvature of the lobe 95a, the line of contact between the two surfaces will be constantly moving, thus minimizing wear in any particular location.

As a result of this design, there is a prompt pivoting movement toward the closed orientation which is initiated as a result of the pressure drop created by the location of the cycloidal surface, and coupled with the provision of the extended hollow region created by the upstanding ridge 103, it is assured that the closing movement is swift and that the amount of regurgitation of blood is minimized. The annular distance that the occluder must travel from the open position to the closed position is of course contingent partially upon the steepness of the angle A of the occluder in the closed position, and this angle can be adapted as desired to obtain a desired effect. Generally, heart valves are made in a variety of sizes which are arbitrarily referred to by the outer diameter of the valve body. For example, for a relatively large valve having a nominal size of 31 millimeters, the angle A may be about 25°, whereas for a smaller valve of for example 27 millimeters, the angle A may be about 27.5°. So as to facilitate relatively uniform surgical practices, it is desirable to keep the overall height of prosthetic valves essentially constant so the choice of the size of valve will be made by the surgeon based upon the diameter alone, and smaller diameter valves may orient the occluder more steeply in the closed position.

Because of the unique noncircular shape of the passageway through the valve 59, it is considered to be especially beneficial for replacement of a mitral valve, as compared to using a round valve such as is commonly being implanted today. The pattern of downstream blood flow from the left atrium into the left ventricle is such that the implantation of a valve having a relatively wide, relatively flat region that mimics the natural configuration of the mitral valve is physiologically superior to a similar valve of a round configuration.

Illustrated in FIGS. 11 through 16 is another alternative embodiment of a heart valve 111 incorporating particular features of the present invention, which valve is designed to provide a particularly wide open central passageway for downstream blood flow through the valve. The valve 111 is referred to as a tri-leaflet valve and has a valve body 113 of annular configuration which is formed with hinge arrangements such as to support three identical leaflets 115 for movement between an open position illustrated in FIG. 11, which permits free downstream flow of blood therethrough, and a closed position shown in FIG. 14 wherein the flow of blood in the reverse or upstream direction is blocked. Although the valve 111 is shown as having a valve body 113 of uniform cylindrical exterior surface 117, it should be understood that it could, if desired, have a groove formed in the exterior surface, as illustrated with respect to valve bodies 13 and 61, to facilitate the installation of a suture ring. The valve body 113 also has an interior surface of generally circular cross-section with the exception of three projections or bosses 121 that project radially thereinto wherein pairs of sockets 123 are constructed which form the receiving halves of the hinge arrangements. As best seen perhaps in FIGS. 12 and 16, the bosses 121 are constructed so as to generally have a pair of angularly oriented side surfaces 125 in which the sockets 123 are formed.

Figure 12:
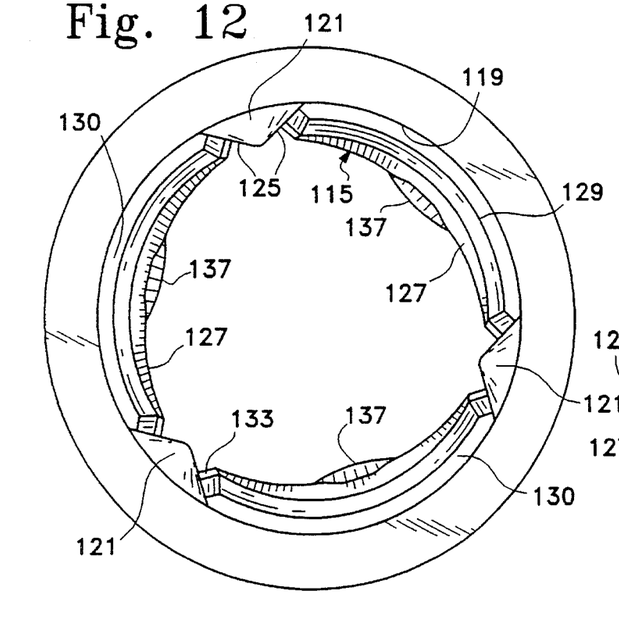
FIG. 12 is a bottom view of the valve shown in FIG. 11, reduced in size, looking through the valve from the upstream end thereof.
Figure 13:
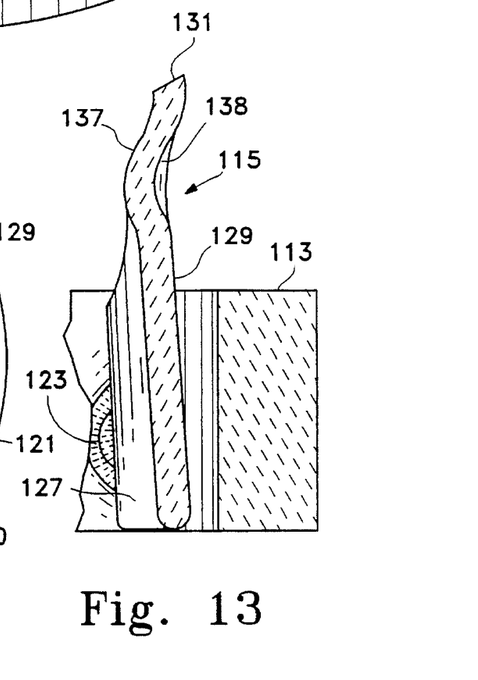
FIG. 13 is a sectional view taken generally along the line 13—13 of FIG. 11, bisecting one of the tri-leaflets in the open position.
Figure 15:
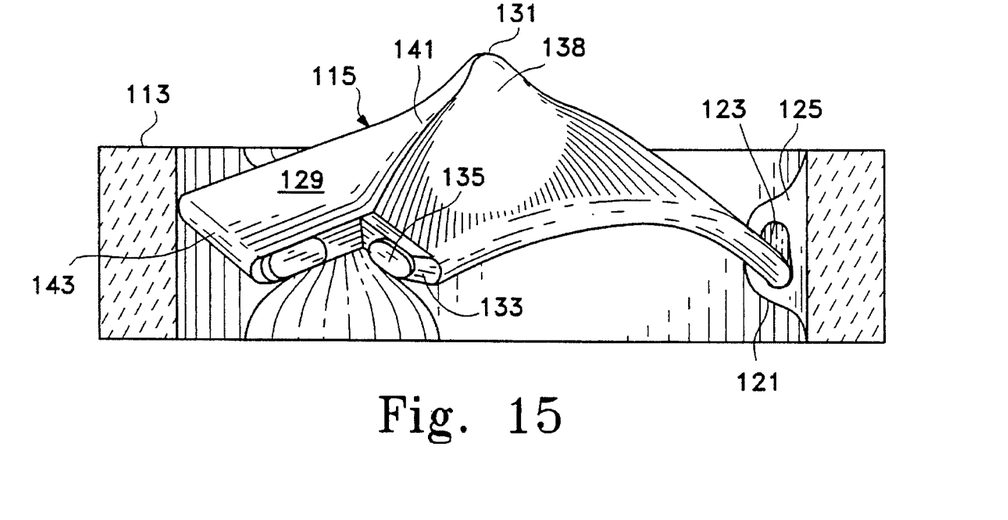
FIG. 15 is a sectional view through the valve in FIG. 14 in the closed position, with the leaflets shown in elevation.

As best seen perhaps in FIG. 13, the leaflets 115 are of uniform thickness, at least throughout their main body portion, and have an inflow surface 127 and an outflow surface 129; the inflow surfaces 127 are the ones which face upstream when the leaflets are in the closed orientation. The main upstream section of the inflow surface 127 is concave, and the corresponding upstream section of the outflow surface 129 is convex. Both of these surfaces are preferably sections of a right circular cylindrical surface having a diameter proportionately less than the diameter of the interior surface 119 of the valve body 113 so that, when the valve is in the open position, as illustrated in FIG. 12, each leaflet 115 is spaced substantially uniformly from the interior surface of the valve body, leaving a narrow arcuate pathway 130 of substantial width wherein blood flows at a sufficient rate to wash the surface and avoid clotting. As best seen perhaps in FIG. 11, each of the leaflets 115 is of generally triangular shape having a vertex 131 which extends directly downstream and a pair of lateral sections 133 at the other remaining two vertices from which oval pegs 135 (FIG. 15) protrude. The pegs 135 protruding from opposite lateral edges of each leaflet are coaxial with each other.

Provided in the downstream region of the inflow surface 127 of each leaflet is a convex surface which is curved in the axial direction, with the leaflet in the open orientation, in a manner which creates a suction effect toward midstream during initial regurgitation flow. This surface 137 is preferably a cycloidal surface 137, and the surface extends to the vertex 131. On the outflow surface of each of the leaflets, the downstream region where the cycloidal surface 137 is located constitutes a hollow 138, which functions in the same manner as the hollow 57 described hereinbefore.

Figure 11:
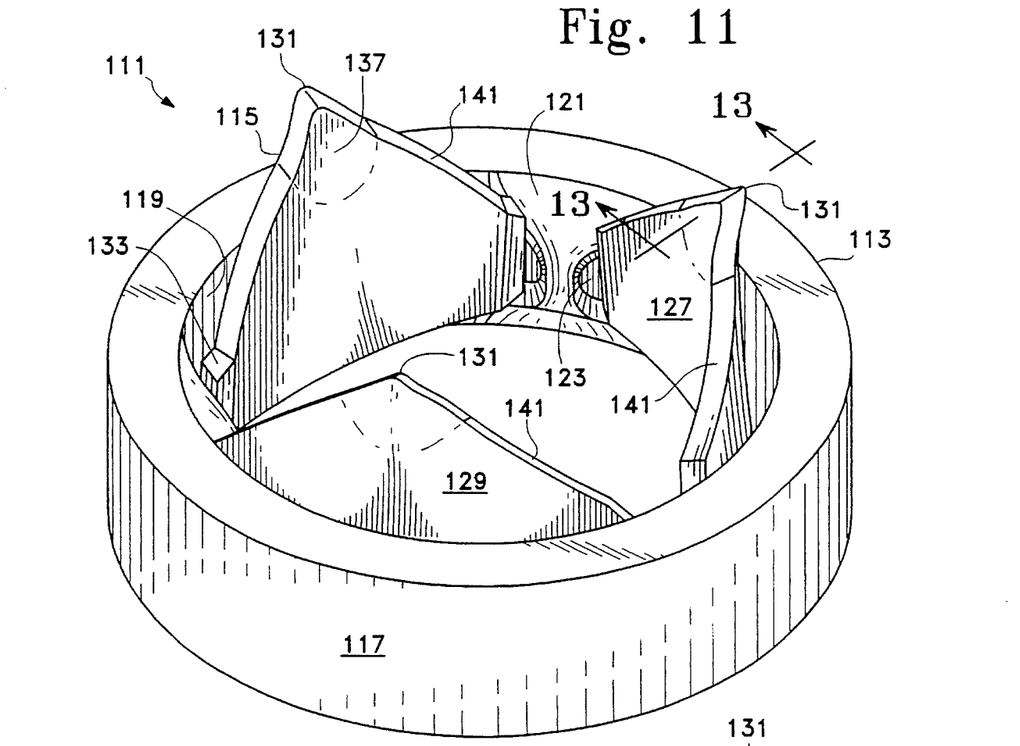
FIG. 11 is a perspective view of a tri-leaflet valve embodying various features of the invention shown in the open position, looking at the downstream end of the valve.
Figure 16:
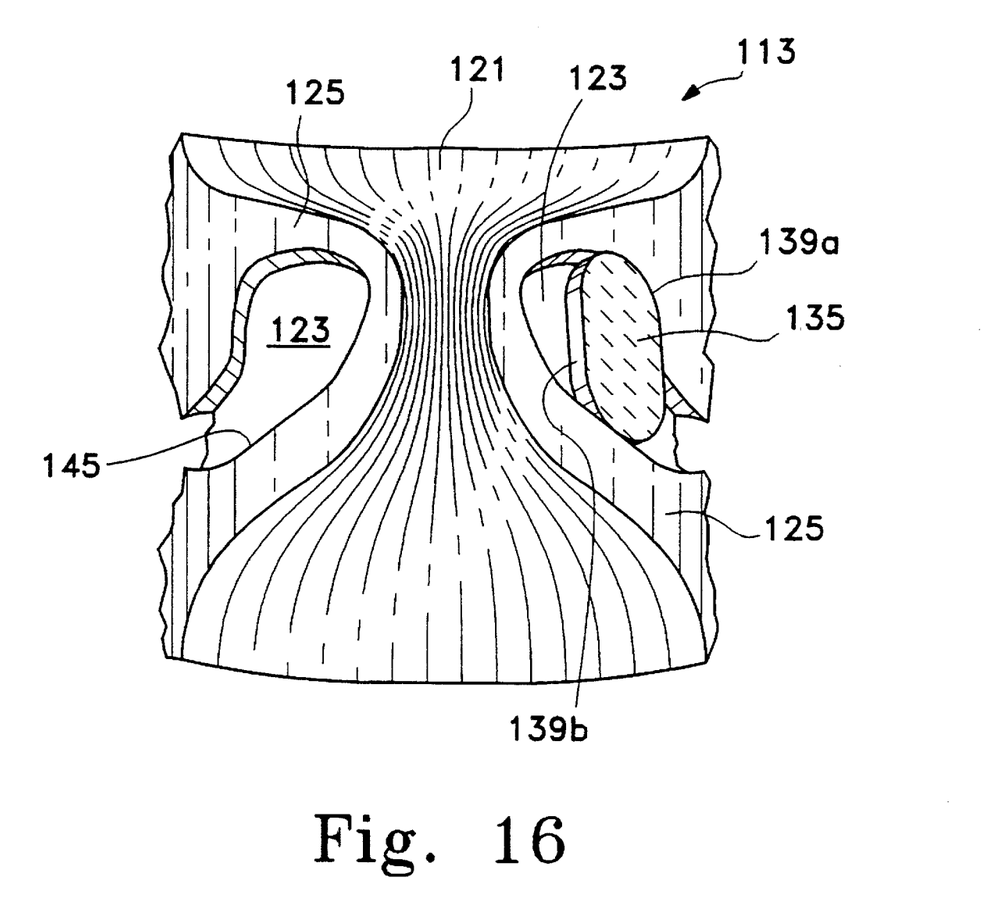
FIG. 16 is a diagrammatic view, enlarged in size, showing a fragment of the valve body as generally seen in FIG. 11 with one of the sockets empty and with the right-hand socket showing an oval protrusion as it would appear with the leaflet in the open position.

When the valve 111 is in its full open position, as shown in FIGS. 11 and 12, the leaflets are oriented generally as shown in FIG. 13 so that the generally rectilinear upstream sections of the inflow and outflow surfaces are aligned at an angle of about 5° from being parallel to the axial centerline through the valve passageway. As previously indicated, if desired, the leaflets could be oriented precisely parallel thereto; however, testing shows they tend to assume an orientation a few degrees from parallel during most rates of blood flow therethrough. Preferably these upstream sections are surfaces of circular cylinders having a radius proportionately less than the radius of the interior surface 119 of the valve body and are oriented in the open position so as to be either coaxial or within about 10° of being coaxial with the centerline of the valve. In this orientation, as best seen in FIG. 12, about 90% of the interior cross-sectional area of the valve passageway is unobstructed and thus available for free flow of blood therethrough. The oval pegs 135 and the sockets 123 can be of substantially the same design as that described in detail with regard to the mitral valve 59. The pivot axis of each leaflet is spaced radially outward from the centerline and preferably is located a distance therefrom equal to at least about 75% of the length of the interior radius of the valve passageway. As shown in FIG. 16, a flat sidewall 139a of the oval peg 135 can be used to abut a flat sidewall section provided in the socket 123 and thus provide a stop for the leaflets in the open position, as earlier explained with regard to the occluder 63.

When blood flow reverses, the flow of blood particles past the centrally located cycloidal downstream regions 137 of the three leaflets causes a pressure drop which creates a force that sucks or pulls the leaflet toward the midstream or center line of the valve passageway. Again, maximum advantage is taken of this force, which is tending to cause the leaflet 115 illustrated in FIG. 13 to rotate counterclockwise, by locating the cycloidal section 137 near the downstream vertex so as to create a large moment arm through which the force acts. Again, once pivoting is initiated as a result of this initial force, the hollow region 138 at the downstream end of the outflow surface 129 moves into full contact with the backflowing blood and assures that swift rotation of each leaflet occurs.

Figure 14:
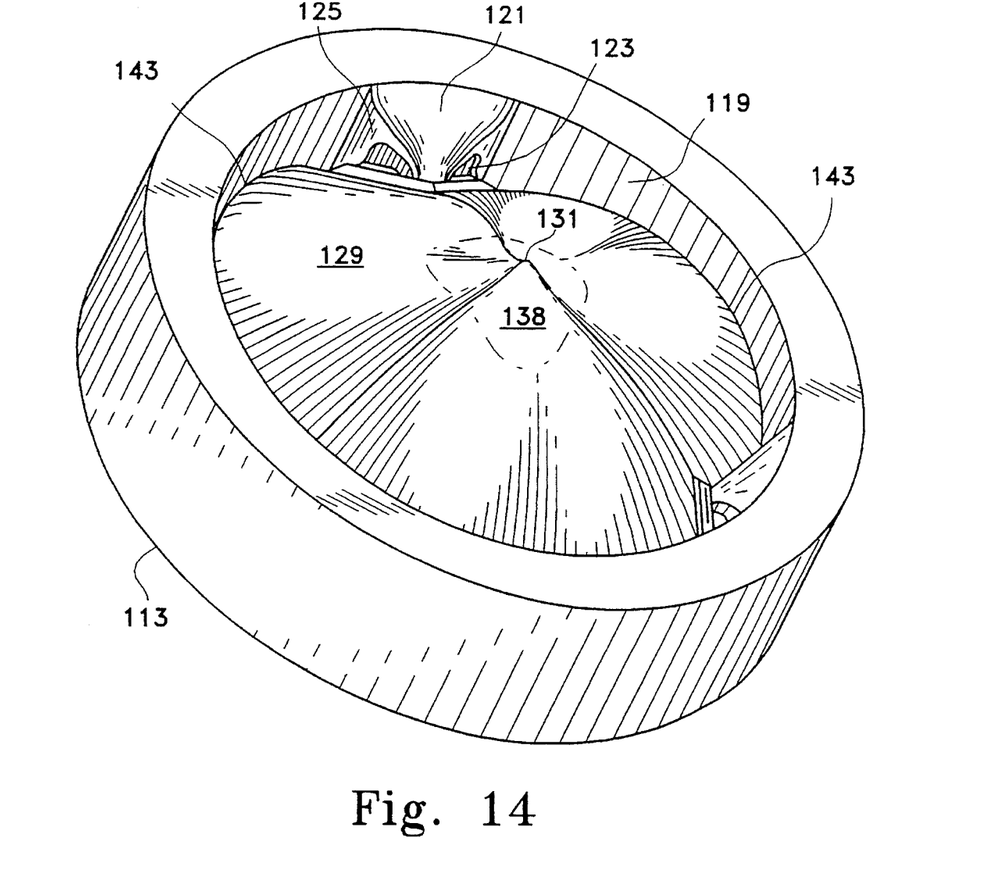
FIG. 14 is a view similar to FIG. 11 showing the valve in the closed position, again viewing the valve from the downstream end.

Each leaflet 115 is formed with a pair of essentially flat side edges 141 which meet at the vertex 131 and with a single upstream arcuate edge 143, which in the closed position as illustrated in FIG. 14, is located in juxtaposition with the right circular cylindrical portion 119 of the interior wall of the valve body 113. The sockets 123 and pegs 135 are preferably also constructed so that the opposite flat sidewall 139b of the oval peg engages a flat section 145 of the socket 123 which serves as a stop for the leaflets in the closed position. As can be seen from FIGS. 14 and 15, in the closed position, the vertices 131 of the three leaflets lie together at the centerline of the valve passageway through the valve body. In this closed orientation, each flat side edge 141 lies in abutting contact with a flat side edge of an adjacent leaflet 115, and the three upstream arcuate edges 143 of the leaflets lie in juxtaposition with the interior surface 119 of the valve body. This arrangement creates a seal about the entire passageway with the exception of some controlled leakage which occurs at the region of the sockets 123, that is designed to provide a cleansing flow which guards against the formation of clotting at these locations.

Although the invention has been described with regard to certain preferred embodiments, which constitute the best mode presently known to the inventor for carrying out this invention, it should be understood that various changes and modifications as would be obvious to one having the ordinary skill in this art may be made without departing from the invention which is defined by the claims appended hereto. For example, although pyrolytic carbon and pyrolytic carbon-coated graphite substrates are the preferred materials from which these valves are made if they are to be employed as prosthetic heart valves, other suitable materials can be employed, and of course if the valves are used for nonmedical applications, strong corrosion-resistant metals may be preferred. Although only prosthetic valves are illustrated, the principles of the construction are considered to be advantageous for incorporation into any fluid-flow check valves. Likewise, although a tri-leaflet valve has been illustrated, it should be understood that similar valves could be constructed having 2, 4, 5 or more leaflets if desired using these same principles.

Particular features of the invention are emphasized in the claims that follow.

What is claimed is:

1. A fluid check valve comprising
   a generally annular valve body having an upstream end and a downstream end which defines a passageway for normal flow of fluid therethrough in a downstream direction,
   occluder means associated with said valve body for movement between an open position and a closed position, in which the open position is oriented up to about 5 percent from an axial centerline for providing minimum obstruction to fluid flow through said valve body, and in which the closed position blocks upstream flow through said valve body,
   said occluder means and said valve body having hinge means for guiding the movement of said occluder means between its open and closed positions,
   said occluder means having a main body section formed with inflow and outflow surfaces of 3-dimensional curvature and also formed with an upstream edge, a downstream edge and two lateral edges,
   said inflow surface of said occluder means in its open position having (a) an upstream section which is concave and has a first radius of curvature in a plane perpendicular to said downstream direction of fluid flow through said passageway and (b) a downstream section which is convex,
   said convex downstream section having a cycloidal curvature in a plane that is parallel to said downstream direction of fluid flow,
   said outflow surface having (c) an upstream section which is convex and (d) a downstream section which includes a shallow concave hollow,
   whereby said cycloidal downstream inflow surface section creates a suction effect during initial upstream flow of fluid that initiates prompt pivoting of said occluder means toward its closed position, while said shallow hollow presents a concave surface against which upstream flow of fluid directly impinges so as to facilitate subsequent rapid closing movement of said occluder means.

2. A valve according to claim 1 wherein said occluder means is of generally uniform thickness throughout a major portion of its main body section, wherein said upstream inflow and outflow surface sections are generally rectilinear in said downstream direction of flow and wherein said cycloidal curvature of said downstream surface section is about a changing radius that is generally shorter than said first radius.

3. A valve according to claim 2 wherein said curvature of said convex downstream inflow surface section is that of a common cycloid.

4. A valve according to claim 3 wherein said hinge means comprises peg means of generally oval cross-sectional shape which protrude in opposite directions from lateral edges of said occluder means and spaced-apart sockets each having at least two lobes are formed in an interior surface of said annular valve body, which sockets receive said peg means and define a pivoting and translational movement of said occluder means between its open and closed positions while allowing said occluder means to open to provide a substantially unobstructed central passageway section for downstream fluid flow.

5. A valve according to claim 4 wherein said sockets are formed with projections separating said two lobes, which projections generally extend toward each other, wherein said oval peg means each have generally parallel flat surface portions which slide on said projections and also have convex ends, and wherein said lobes have concave curved surfaces which are shaped so that there is sliding contact between said convex end surfaces of said oval peg means and said concave surfaces of said lobes during said pivoting-translational movement of said occluder means.

6. A valve according to claim 4 wherein said occluder means comprises a single occluder and wherein said sockets are located in said valve body to define a pivot axis located so that, when said single occluder is oriented in its open position, said generally rectilinear upstream inflow and outflow surfaces are oriented substantially parallel to said downstream direction of fluid flow and an unobstructed central passageway is provided which is equal to at least about 80% of the cross-sectional area of said valve passageway.

7. A heart valve prosthesis comprising
   a generally annular valve body having an upstream end and a downstream end which defines a passageway extending therethrough for the flow of blood in a downstream direction,
   a single occluder associated with said valve body for movement between an open position and a closed position, in which the open position is oriented up to about 5 percent from an axial centerline for providing minimum obstruction to blood flow through said valve body, and in which the closed position blocks upstream flow of blood through said valve body,
   said occluder and said valve body having hinge means for guiding the movement of said occluder between its open and closed positions,
   said occluder having a main body section formed with a minor arcuate upstream edge, as oriented in the open position, and a major arcuate downstream edge, both said arcuate edges being in juxtaposed sealing locations with respective regions of said valve body in the closed position,
   said occluder main body section also having inflow and outflow surfaces of 3-dimensional curvature, said inflow surface of said occluder in its open position having (a) an upstream section which is concave and has a first radius of curvature in a plane perpendicular to said downstream direction of blood flow and (b) a downstream section which is convex, said convex downstream section having a cycloidal curvature in a plane that is parallel to said downstream direction of blood flow, which curvature is such that its radius of curvature at any location therealong is shorter than said first radius, said outflow surface having (c) an upstream section which is convex and (d) a downstream section which includes a shallow concave hollow, whereby said convex cycloidal downstream inflow surface section creates a suction effect during initial upstream flow of blood which initiates prompt pivoting of said occluder toward its closed position and said shallow hollow presents a concave surface against which upstream flow of blood directly impinges so as to facilitate subsequent rapid closing movement of said occluder.

8. A heart valve prosthesis according to claim 7 wherein said occluder is of generally uniform thickness throughout at least a major portion of its main body section.

9. A heart valve prosthesis according to claim 7 wherein said curvature of said convex downstream section is that of a common cycloid.

10. A heart valve prosthesis according to claim 9 wherein said hinge means comprises pegs of generally oval cross-sectional shape, having two flat parallel surface portions and two convex end surface portions, which pegs protrude from lateral edges of said occluder that are located respectively between said major and minor arcuate edges, and a pair of sockets each having at least two lobes, which sockets are formed in said valve body so as to receive said pegs and define said pivoting-translational movement of said single occluder.

11. A heart valve prosthesis according to claim 10 wherein said sockets are formed with projections separating said lobes on which projections said flat surface portions of said oval pegs slide, and wherein said lobes have concave surfaces shaped with a radius of curvature greater than that of said convex end surface portions so that there is moving contact between said convex surface portions of said oval pegs and said concave surfaces of said lobes during opening and closing movement of said occluder.

12. A heart valve prosthesis according to claim 10 wherein said sockets are formed in an interior surface of said annular heart valve body in a location to define a pivot axis so located that, when said occluder is in its open orientation, an unobstructed central flow passageway is created which is equal to at least about 85% of the cross-sectional area of said valve passageway through said valve body in the plane of said valve body.

13. A heart valve according to claim 7 designed as a mitral valve replacement, wherein said valve body defines an interior passageway of noncircular cross section, said body, in plan, having a straight minor section, a major section that is generally semicircular and a pair of arcuate connecting sections, and wherein said hinge means are located in said connecting sections and are constructed so that said occluder moves about a shifting pivot axis that remains substantially parallel to said straight minor section of said valve body passageway.

14. A heart valve according to claim 13 wherein said outflow surface upstream section of said occluder in its open position is generally rectilinear in said downstream direction of flow and said outflow surface includes an upstanding arcuate ridge at the boundary between said concave hollow and said upstream convex outflow surface section, which ridge protrudes beyond the level of said generally rectilinear upstream outflow surface section.

15. A heart valve prosthesis comprising a generally annular valve body having an upstream end and a downstream end which defines a passageway extending therethrough for the flow of blood in a downstream direction, a single occluder associated with said valve body for movement between an open position and a closed position, in which the open position is oriented up to about 5 percent from an axial centerline for providing minimum obstruction to blood flow through said valve body, and in which the closed position blocks upstream flow of blood through said valve body, said occluder and said valve body having hinge means for guiding the movement of said occluder between its open and closed positions, said occluder having a main body section formed with a minor arcuate upstream edge, as oriented in the open position, and a major arcuate downstream edge, both said arcuate edges being in juxtaposed sealing locations with respective regions of said valve body in the closed position, said occluder main body section also having inflow and outflow surfaces, with major portions of said surfaces being generally rectilinear and curved in a plane perpendicular to said downstream direction of blood flow when said occluder is in its open position, said inflow surface of said occluder in its open position having (a) an upstream section which is concave and has a first radius of curvature and (b) a downstream section which is convex and which has a cycloidal curvature in a plane parallel to said downstream direction of blood flow, which cycloidal curvature is such that its radius of curvature at any location therealong is shorter than said first radius, said outflow surface having (c) an upstream section which is convex and (d) a downstream section which includes a shallow concave hollow, said hinge means permitting said occluder to assume an orientation in its open position with said generally rectilinear surfaces oriented substantially parallel to said downstream direction of flow, whereby said convex cycloidal downstream inflow surface section creates a suction effect during initial upstream flow of blood which initiates prompt pivoting of said occluder toward its closed position and said shallow hollow presents a concave surface against which upstream flow of blood directly impinges so as to facilitate subsequent rapid closing movement of said occluder.

16. A heart valve prosthesis according to claim 15 wherein said occluder is of generally uniform thickness throughout at least a major portion of its main body section and wherein said concave hollow lies directly opposite of said convex cycloidal section.

17. A heart valve according to claim 16 designed as a mitral valve replacement, wherein said valve body defines an interior passageway of noncircular cross section, said body, in plan, having a straight minor section, a major section that is generally semicircular and a pair of arcuate connecting sections, and wherein said hinge means are located in said connecting sections and are constructed so that said occluder moves about a shifting pivot axis which always remains substantially parallel to said straight minor section of said valve body.

18. A heart valve according to claim 17 wherein said outflow surface of said occluder includes an upstanding arcuate ridge at the boundary between said concave hollow and said generally rectilinear upstream convex section, which ridge protrudes beyond the level of said generally rectilinear upstream outflow surface section.

19. A heart valve prosthesis according to claim 18 wherein said curvature of said convex downstream section is that of a common cycloid.

20. A heart valve prosthesis according to claim 19 wherein portions of said hinge means are formed in said valve body in a location to define a pivot axis so located that, when said occluder is in its open orientation, an unobstructed central flow passageway is created equal to at least about 85% of the cross-sectional area of said valve passageway through said valve body in the plane of said valve body.

* * * * *